United States Patent [19]

Holtermann

[11] Patent Number: 5,180,377
[45] Date of Patent: Jan. 19, 1993

[54] OSTOMY APPLIANCE

[75] Inventor: Henri Holtermann, Saint Jean de Luz, France

[73] Assignee: Laboratoires Biotrol, Paris, France

[21] Appl. No.: 606,610

[22] Filed: Oct. 31, 1990

[30] Foreign Application Priority Data

Nov. 13, 1989 [FR] France .................. 89 14834

[51] Int. Cl.⁵ .............................. A61F 5/44
[52] U.S. Cl. ........................ 604/342; 604/338
[58] Field of Search ............. 604/332–345; 24/19, 269, 274 R

[56] References Cited

U.S. PATENT DOCUMENTS

| | | |
|---|---|---|
| 1,689,085 | 10/1928 | Teves . |
| 3,964,485 | 9/1974 | Neumeier . |
| 4,546,524 | 10/1985 | Kreft ........................ 24/269 |
| 4,834,731 | 5/1989 | Nowak et al. ............. 604/336 |
| 4,872,869 | 10/1989 | Johns ........................ 604/339 |
| 5,026,360 | 6/1991 | Johnsen et al. ........... 604/338 |

FOREIGN PATENT DOCUMENTS

| | | |
|---|---|---|
| 0171255 | 2/1986 | European Pat. Off. . |
| 284947 | 7/1913 | Fed. Rep. of Germany . |
| 2626464 | 8/1989 | France . |
| 2217207 | 10/1989 | United Kingdom . |
| 9101118 | 2/1991 | World Int. Prop. O. ..... 604/342 |

*Primary Examiner*—Ronald Frinks
*Assistant Examiner*—R. Clarke
*Attorney, Agent, or Firm*—Oblon, Spivak, McClelland, Maier & Neustadt

[57] ABSTRACT

An ostomy appliance is disclosed, which includes a front plate or pouch-holder intended to be fixed about an artificial opening in the body of a user by an adhesive pressure sensitive shoe, a belt or similar, as well as a pouch for collecting body fluids and/or waste adapted to be removably assembled with the pouch-holder by a nose of the pouch and which is provided for cooperating with an end-piece fast with the plate and which surrounds the stoma in its condition of use, the assembly of the pouch nose and the end-piece resulting from the clamping effect of a deformable member, further including a control mechanism associated with the pouch-holder and separate from the member, the latter being also associated with the pouch-holder and adapted to cooperate directly with the pouch nose having a shape and being dimensioned such that a sealed mechanical connection of the pouch nose and the end-piece is produced in response to actuation of the mechanism.

20 Claims, 6 Drawing Sheets

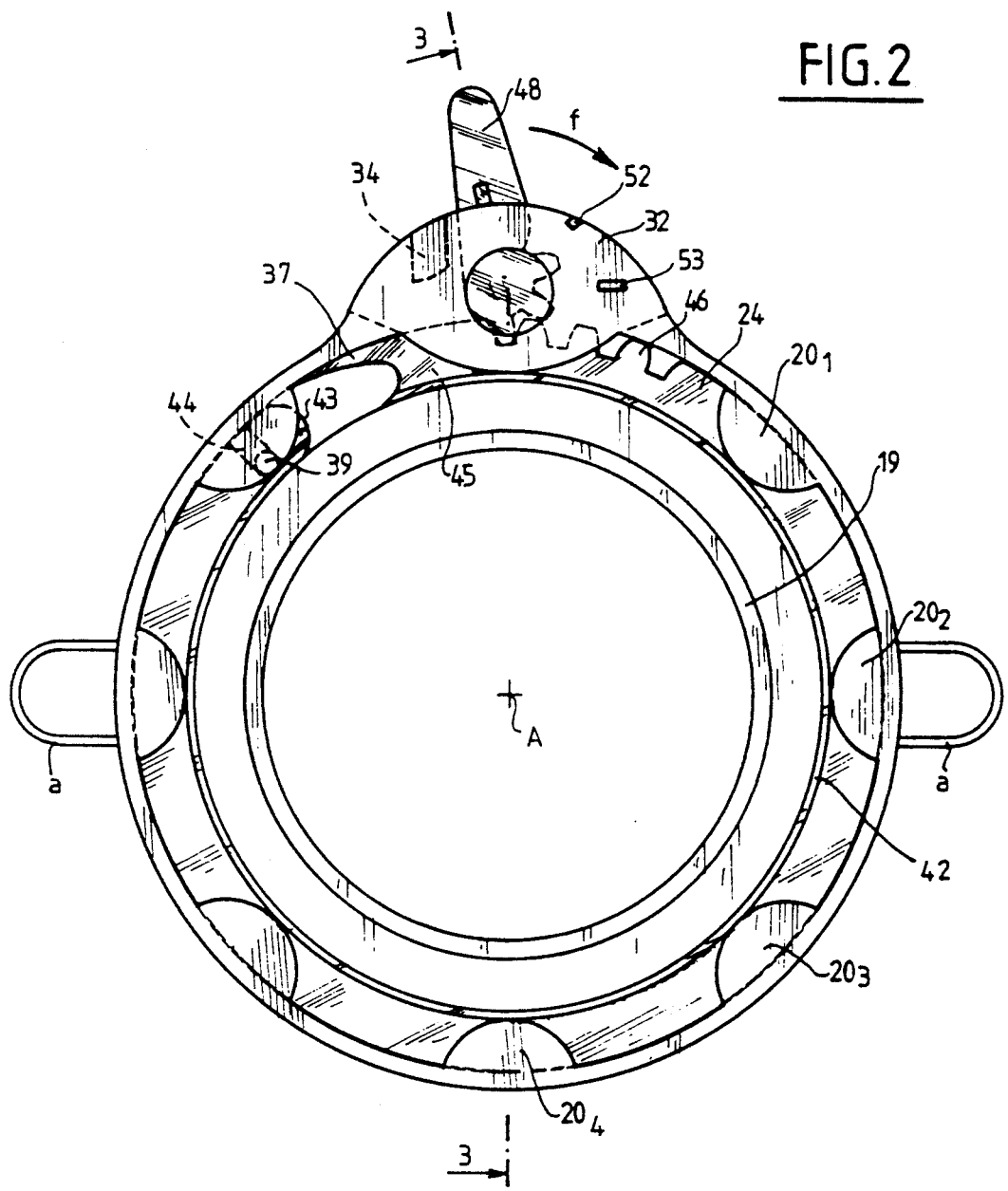

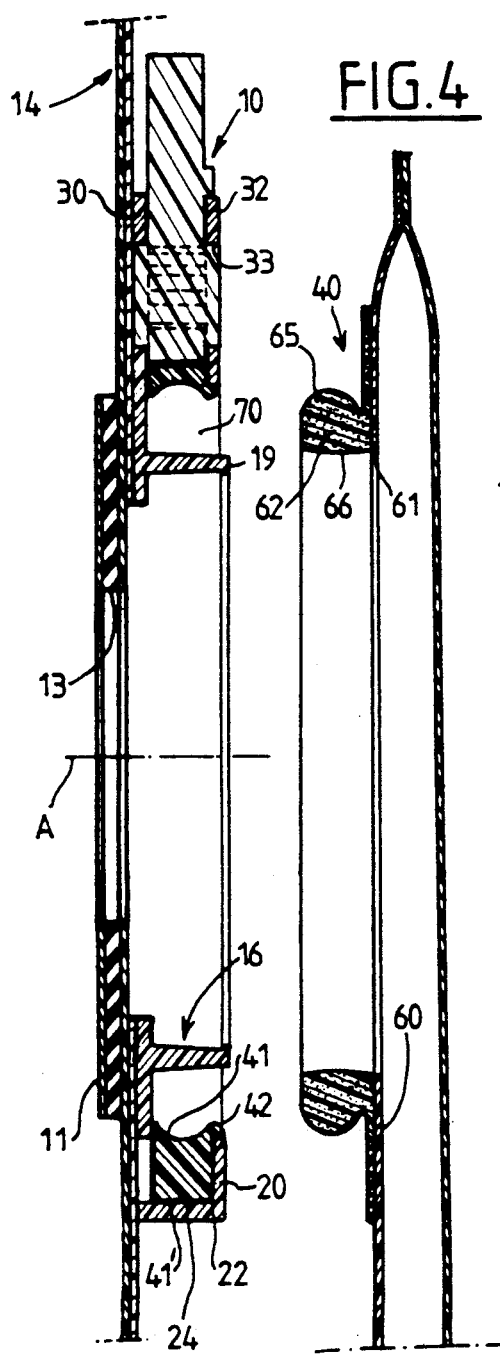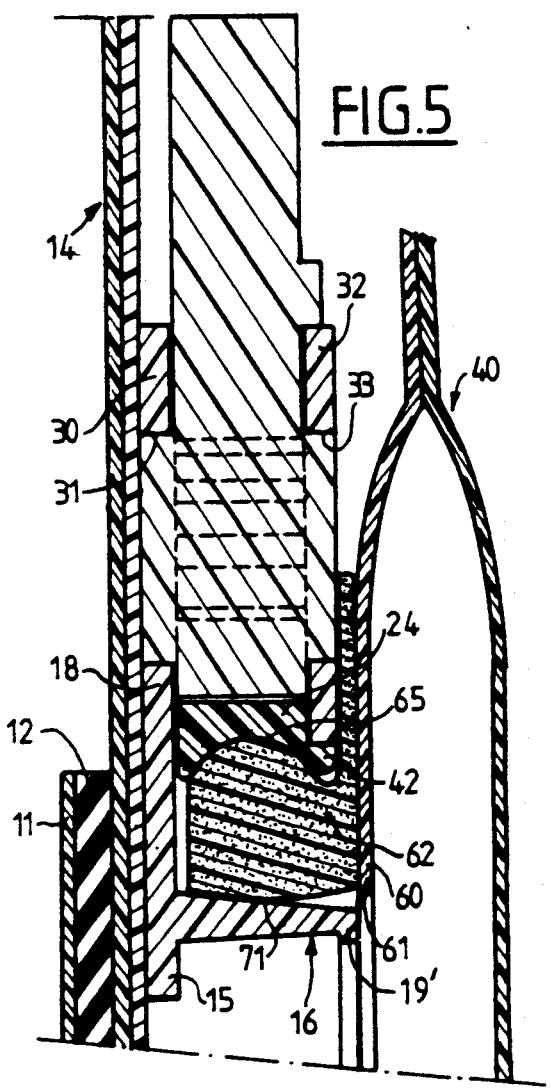

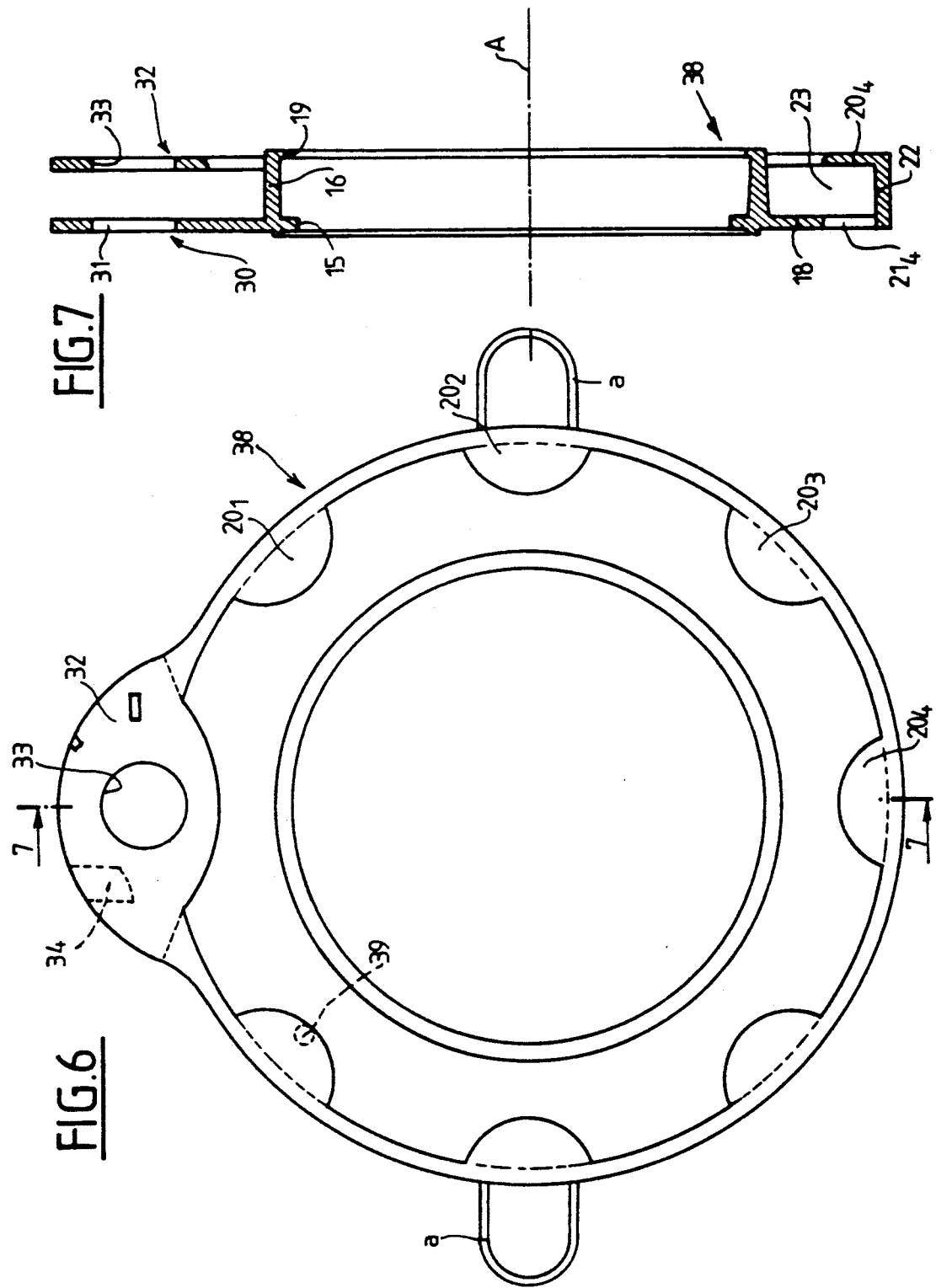

OSTOMY APPLIANCE

BACKGROUND OF THE INVENTION

Field of the Invention

The present invention relates to an ostomy appliance.

DISCUSSION OF THE BACKGROUND

As excellently explained in the work by H. BAUMEL and J. F. LOUIS "Vivre avec une stomie digestive ou urinaire" (Simep, Villeurbanne, Paris, 1986): "The loss of intestinal or urinary incontinence following the creation of a stoma or opening can only be compensated for by wearing an appliance for collecting the material or urine". Numerous appliances have consequently been proposed for a long time for such collection and the above mentioned work distinguishes three great varieties, not only for enterostomy (illeostomy, colostomy, ... ) but also for urostomy, namely devices formed by pouches used once and fixed directly to the skin of the user by a ring shaped adhesive, or such pouches having a cutaneous protector, or else "two part" systems in which the collecting pouch—in the form of a disposable or emptyable bag—may be removably fixed to a front protective plate fixed to the body of the user by an adhesive shoe or by a belt.

Systems of the last mentioned type must satisfy imperative conditions some of which are contradictory. The collecting pouch must in face be fixed to the front protecting late or pouch-holder without applying appreciable pressure in the zone adjacent the stoma or opening—which is sensitive and generally painful—and fixing must be reliable with perfect sealing of the assembly of the system while allowing ready but not untimely separation of the pouch. Complementarily, the appliance must not cause peristomial cutaneous complications, must be as discreet as possible and be adaptable to patients of very different morphologies. It is further desirable that, after apprenticeship by the attendant personnel, for the patients to be able to position the collecting pouches on the pouch-holder themselves, which of course means, and particularly for user of a certain age, that the manipulations for assembling and separating the pouch and the pouch-holder must be as simple and easy as possible.

Thus, to attempt to bring a solution to the problem raised, a "two part" system has recently been proposed, for example in FR-A1-2 626 464, in which the means for coupling the pouch and the pouch-holder together are formed by a deformable collar and a split ring adapted for clamping the periphery of this collar, a tube having an external dimension substantially equal to the internal dimension of the collar being inserted or withdrawn by sliding in the collar when the ring is in an open position, so that, when the ring is in the position clamped about the collar, the latter is deformed about the tube Actuation of this split ring is relatively difficult, on the one hand, and the construction of the assembly is relatively complex, on the other hand, since the diameters of the tube and of the collar must be formed with very small dimensional tolerances so that the sealed assembly is obtained by reduced deformation of the collar whose U shaped section normally forms an obstacle to such deformation.

It will then be readily understood that, notwithstanding the very numerous systems proposed of the fit-on type, such for example as that described in EP-A-0 171,255, or of the type described above or else of the type according to GB-A2 217 207 in which a clamping ring cooperates with end-pieces of mating shapes of the pouch and of the pouch-holder, the problem still exists of providing an improved ostomy appliance which allows the different requirements to be met for such appliances.

SUMMARY OF THE INVENTION

It is consequently an object of the invention to provide such an appliance which is applicable to digestive or urinary stoma, which satisfies such conditions and which is further sufficiently simple so as to be not of a prohibitive cost.

It is also an object of the invention to provide such as appliance which makes it possible to readily modify the relative position of the collecting ouch and of the pouch-holder without risk for the patient.

A further object of the invention is to provide such an appliance in which positioning of the pouch on the front plate or pouch-holder previously fixed to the body of the user is extremely easy, on the other hand, and in which, on the other hand, a slight inaccuracy of fitting the pouch on the pouch-holder is automatically corrected whereas a greater inaccuracy prevents defective fixing and the prejudicial consequences which might result therefrom for the patient.

The problem is solved, in an ostomy appliance of the present invention comprising a front plate or pouch-holder intended to be fixed about an artificial opening in the body of a user by means of an adhesive pressure sensitive shoe, a belt or similar structure, as well as a pouch for collecting body fluids and/or waste adapted to be removably assembled with the pouch-holder by a nose member which it comprises and which is provided for cooperating with an end-piece fast with the plate and which surrounds the stoma in its condition of use, the assembly of the pouch nose and the end-piece resulting from the clamping effect of a deformable member, by the fact that the appliance comprises a control mechanism associated with the pouch-holder and separate from said member, this latter being also associated with the pouch-holder and adapted to cooperate directly with the pouch nose having a shape and dimensions such that it produces a sealed mechanical connection of the pouch nose and the end-piece in response to actuation of said mechanism.

In a preferred embodiment, the clamping member is includes a ring portion and the mechanism associated with the pouch-holder is adapted for bringing one of the ends of said member close to the other end from which it was initially remote.

According to another characteristic of the invention, the pouch nose is advantageously formed by moulding one or more plastic materials, preferably with an ethylene and vinyl acetate copolymer (EVA) base or from a compressible polymer material, such as a polyurethane foam or else, and preferably, from a cellular material with integrated surface skin, for example with a polyethylene or ethylene and vinyl acetate copolymer, or polyurethane base.

The ostomy appliance according to the invention is then characterized in that it is formed, although belonging to the type of "two part" systems, by at least three plastic material elements, namely a pouch-holder comprising a relatively rigid end-piece, to which may be assembled a pouch with a flexible pouch nose which is resiliently deformable under the clamping action of a member acting to immobilize the pouch nose with respect to the end-piece by an effect of mating forms in response to the actuation of an appropriate control member.

In a first embodiment, the mechanism for actuating the clamping member, for bringing together the initially remote ends of said member, is of the articulated lever type.

In another embodiment, the mechanism for brining together the two ends of an clamping member is of the excentric type or similar structure.

In another embodiment, said actuating mechanism is of the mesh type which teeth at one end of the clamping member and teeth of a mating form being provided on a lever mounted for pivoting on a part for holding said member in position.

Whatever the embodiment, the invention guarantees sealing of the junction between the pouch nose and the pouch-holder by at least a linear type contact between the external surface of the end-piece integral with the pouch-holder and the internal surface of the pouch nose and, for providing such linear contact, the end-piece of the pouch-holder and the pouch nose have appropriate geometric shapes, for example a truncated cone shaped for the end-piece and bellied for the pouch nose, or vice versa.

To guarantee that the pouch is reliably held on the pouch-holder as long as the pouch is not to be changed, locking means are associated with the mechanism for bringing the two end portions of the clamping member together.

The fact that the cross section of the pouch nose and said member are mating, also contributes to the operating safety of the appliance, since actuation of the mechanism brining the ends of the clamping member together is impossible as long as the pouch nose is not correctly positioned with respect to the clamping member and to the end-piece of the pouch-holder, whereas, for substantially satisfactory positioning, the beginning of actuation of said mechanism causes, by a guidance effect, perfect positioning of the component parts of the appliance with respect to each other until said portions are locked together by a mating shape effect.

The invention also relates to a body waste and/or fluid collecting pouch, particularly for enterostomy or urostomy entering into the construction of an appliance such as defined above and characterized in that it comprises, about an opening in one of its walls, a pouch nose made from a flexible resiliently deformable material and whose cross section mates with that of the clamping member, on the one hand, and paired with that of the end-piece of the pouch-holder, on the other hand, to provide the sealing connection between pouch and pouch-holder.

The invention also relates to a front plate or pouch-holder entering into the construction of the appliance such as defined above, comprising a pressure sensitive adhesive shoe, belt or similar means for fixing to the body of a user with a part comprising an end-piece for assembling a body waste and/or fluid collecting pouch and which is characterized in that said part is adapted for holding a clamping member in position which is made operative when an appropriate mechanism is actuated after a pouch has been placed on the pouch-holder with its nose housed between said end-piece and said member.

In a preferred embodiment, the clamping member is held in position on said part by being housed between a base or radial collar, external to the end-piece and a sleeve with bent back portions directed substantially parallel to the collar.

In an advantageous embodiment of the pouch-holder, the end-piece, its collar, the sleeve and the bends for holding the clamping member in position are molded in a single piece and the end-piece is shaped at its end remote form the adhesive shoe as a flange for mounting and holding a ring in position having a particularly useful convexity for use with an invaginated stoma.

In a particularly preferred embodiment, the actuating member is a pivoting lever having a set of teeth cooperating with teeth of a mating shape formed on the external surface of the clamping member and said lever is mounted for pivoting about an axis materialized by two studs which it carries and which are engaged in eyes of mating shapes of two radially projecting cheeks of said part.

BRIEF DESCRIPTION OF THE DRAWINGS

The invention will be better understood from the following description, given by way of example with reference to the accompanying drawings in which:

FIG. 2 is an elevational view of the pouch-holder and of a clamping member which it contains;

FIG. 3 is a sectional view through line 3—3 of FIG. 2;

FIG. 4 is a schematic sectional view of an appliance pouch according to the invention;

FIG. 5 is a partial view on a larger scale of an appliance according to the invention in the assembled position of the pouch on the pouch-holder;

FIG. 6 is a view of a component part of the pouch-holder;

FIG. 7 is a sectional view through line 7—7 of FIG. 6;

DESCRIPTION OF THE PREFERRED EMBODIMENTS

Figure 1B:
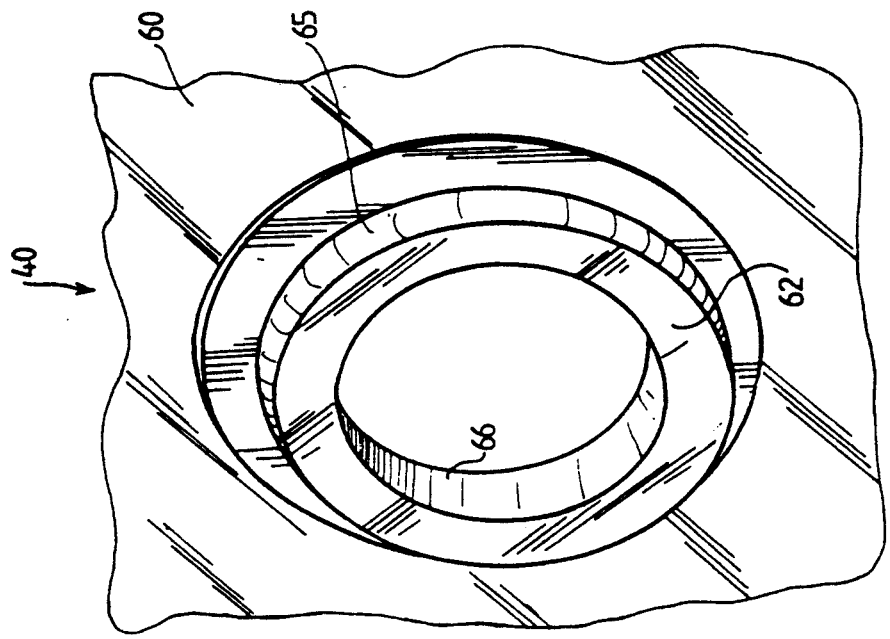
FIG. 1 is a schematic perspective view showing, distant from each other, a front plate or pouch-holder and a pouch nose of an appliance according to the invention.
Figure 1A:
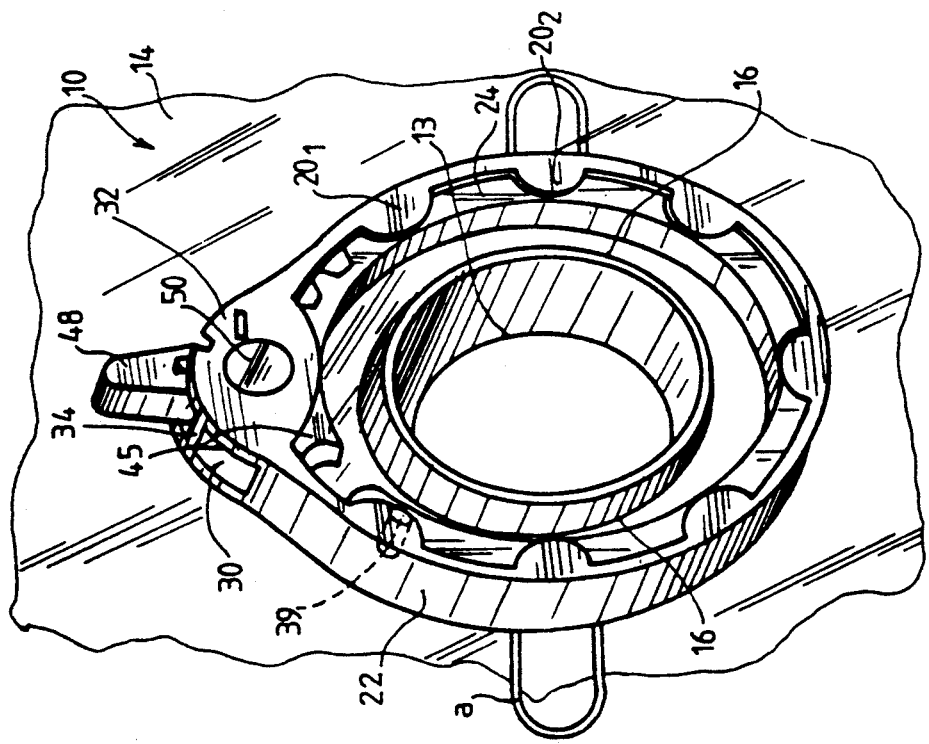

Reference will be made first of all to FIGS. 1 to 11. They show an ostomy appliance according to the invention of the "two part" type, i.e. comprising a front plate or pouch-holder 10 adapted to be fixed about an artificial opening in the body of a user by means of an appropriate fixing means such as a pressure sensitive adhesive shoe 12, known per se, and which is protected by a film 11, FIGS. 3 and 5, which may be stripped off. In a variant and/or complimentary embodiment, the pouch-holder 10 may be held in position on the body of the user by means of a belt (not shown) or a similar means adapted to be fixed by small loops a.

The pouch-holder 10, whose adhesive shoe 12 has an opening 13 surrounding the stoma in its condition of use, also comprises, on the face of the adhesive 12 opposite that coming into contact with the body of the user, a composite foil 14 which contributes to protecting the peristomial zone and for holding it in position on the skin of the user. On the face of the composite foil 14 opposite that connecting tot he shoe 12 a moulded plastic material end-piece 16 that is fixed by an internal ring 15 which it comprises, Fixing may be by welding, for example of the thermal type or high frequency type or by bonding with or without interpositioning of film(s) compatible with the materials forming an end-piece and the foil 14, which may be made from high or low density polyethylene, or from ethylene and vinyl acetate copolymer (EVA) or from polyvinyl chloride (PVC) or from polyamide or mixture of these materials, the film of the composite foil 14 adjacent ring 15 being advantageously a non woven film having a basis of one or more of these materials.

End-piece 16 projects from a base 18 having the general shape of a circular collar, substantially coplanar with ring 15 and is shaped as a truncated cone shaped surface inclined progressively towards the axis A of the device with, on its free edge 19, a flange 19' for mounting and holding in position a ring or cup, not shown, having a convexity particularly useful with certain invaginated stoma. As can be clearly seen in FIGS. 1, 6 and 7, the end-piece 16 with a circular contour is surrounded at a distance by a cylindrical wall 22 which forms a space 23 with the end-piece, the free edge of wall 22 not having a circular contour (facing axis A) but being cut out with lobes $20_1$, $20_2$, $20_3$, etc . . . evenly spaced apart from axis A, facing holes 21 formed with the same arrangement in base 18.

According to the invention, space 23 is provided for housing a clamping member 24, FIG. 8, which is advantageously moulded from a plastic material in the circular form and "open" position; which is that shown in the drawing of FIG. 8 so that a resilient spring effect results when its ends, which have been previously brought together, are released to move away from each other, as will be explained further on.

As is also clearly shown in FIGS. 1, 2, 6 and 7, base 18 has a first radial lug 30 pierced with an orifice 31 and, facing it and substantially in the plane of flange 19' and lobes 20, a second lug 32 is provided pierced with an orifice 33, lugs 30 and 32 being connected together by a narrow bridge 34.

Figure 8:
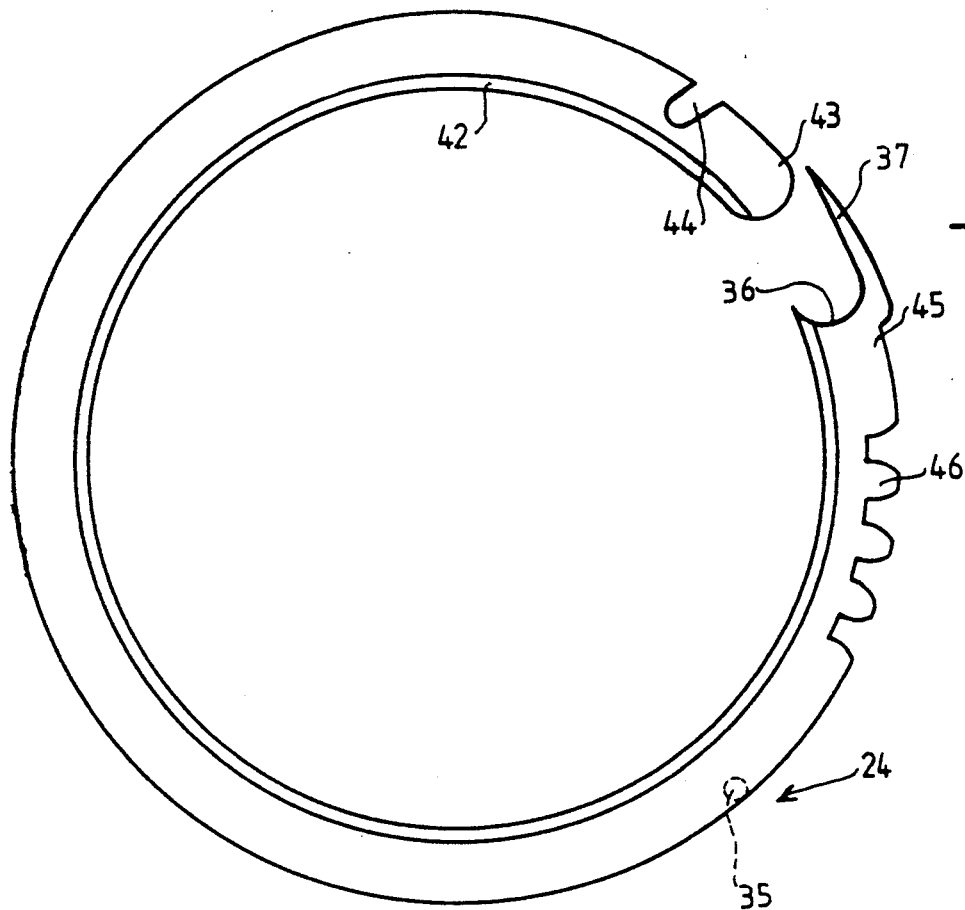
FIG. 8 is an elevational view of a clamping member of a device according to the invention.
Figure 11:
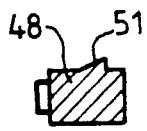
FIG. 11 is a sectional view through line 11—11 of FIG. 9.
Figure 9:
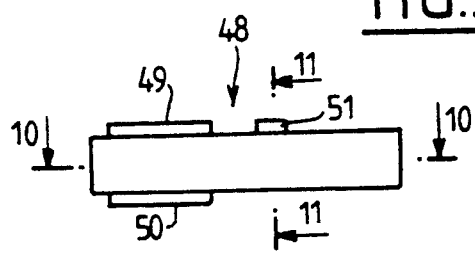
FIG. 9 is an elevational view of an actuating lever.
Figure 10:
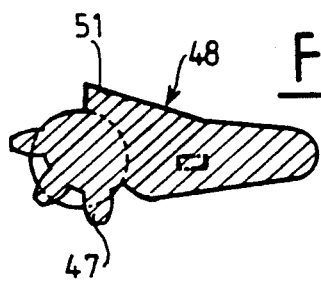
FIG. 10 is a sectional view through line 10—10 of FIG. 9.

As shown in FIGS. 2, 5 and 8, the member 24 (advantageously made from polypropylene, polyamide, copolymerized ABS or high density polyethylene) is formed by a ring portion made from a resiliently deformable plastic material and it has a cross section with concave internal surface 41 and cylindrical external surface 41' with a cord 42 which may come into contact with the nearest portions of the axis A of lobes 20. In the vicinity of one of its ends 43, member 24 has an oblong hole 44 adapted to cooperate with a pin 39 projecting from base 18 for holding this end 43 in position, whereas the other end 45 of member 24 is shaped as a beak 37 and a concave recess 36 which, when the ends 43 and 45 are brought together, give to member 24 a very substantially circular shape. A stud 35 on the face of member 24 opposite that with cord 42 is housed in one of the holes 21 for peripheral positioning of member 24 which also has, in the vicinity of its end 45 and on its external surface, teeth 46 with which are adapted to mesh the teeth of mating shape and pitch 47 of a lever 48 mounted for pivoting by its journals 49 and 50, see FIG. 9, in orifices 31 and 33 of lugs 30 and 32 respectively. For maintaining the clamping effect introduced by member 24 when lever 48 is actuated in the direction of arrow f, see FIG. 2, thus causing the ends 43 and 45 to draw together, in one embodiment it is provided for one of the faces of lever 48 to be provided with a spur 51, adapted for cooperating with matching notches 52 and 53 provided on one of the lugs, for example lug 32, of part 38 formed by the one piece assembly of end-piece 16, base 18, the cylindrical wall 22, lobes 20, ring 15 and said lugs and possibly loops a.

In a variant, a spur 51' is formed on the front face of the lever and maintenance of the clamping effect is obtained by locking said spur in contact with bridge 34, after passing over the latter.

The ostomy appliance according to the invention also comprises a pouch 40 of the type to be thrown away or emptied for collecting body fluids and/or waste to be removed through the end-piece 16. It may be made from a polyethylene or PVC or polyamide film or from a complex barrier film of polyethylene/EVA/polyvinyl chloride /EVA/polyethylene type, such as those under the registered trademark SARANEX by the firm DOW CHEMICAL or a complex film of EVA/vinylidene polychloride-EVA copolymer, such as those known under the trademark CRYOVAC by the firm GRACE and under the registered trademark SARANEX by the firm DOW CHEMICAL or else a complex film of EVA/EVOH/EVA type or a similar material.

According to the invention, with pouch 40, which comprises a wall 60 formed with a hole 61, is associated a collection or ouch nose 62 fixed sealingly to pouch 40 on which it is welded, or bonded, as mentioned above, so that its axis is coaxial with that of hole 61. As can be clearly seen in FIGS. 4 and 5, the connection or pouch nose 62 is shaped with an external lateral surface 65, having the same profile as the internal surface of member 24 and a curved or convex internal surface 66. Also according to the invention, the pouch nose 62 is made from a flexible material, advantageously a cellulose plastic material, preferably with an ethylene and vinyl acetate copolymer (EVA) base or from a compressible polymer material, such as a polyurethane foam or else, and preferably, from a cellular material with integrated surface skin, for example, with a poyethylene or ethylene and vinyl acetate copolymer, or polyurethane base, so that, and contrary to known devices, the pouch nose may be deformed, even bent, for facilitating positioning thereof on the front plate or pouch-holder 10.

Operation of the appliance according to the invention follows immediately from the foregoing.

The pouch-holder 10 (i.e. the assembly formed by part 38, its means for fixing to the body of the user, member 24 and its actuating mechanism) being fixed to the body of the user, for example by means of a belt and loops a and/or by the adhesive effect of shoe 12 and foil 14 (after the protective film 11 of course has been removed), lever 48 is in the condition shown in FIG. 2, in which its teeth 47 cooperate with the teeth 46 of member 24 whose ends 43 and 45 are then distant from each other. In this condition, pouch 40 may be presented opposite the pouch-holder and the flexible pouch nose 62 introduced without effort and without difficulty into the annular space 70, FIG. 3, existing between the external lateral surface of end-piece 16 and the internal lateral surface 41 of member 24. When, from this condition, lever 48 is pivoted in the direction of arrow f shown in FIG. 2, the diameter of member 24 is reduced—the ends 43 and 45 being brought close together- —and the result is a force clamping said member on the connection or pouch nose 62 which immobilizes or locks the pouch on the pouch-holder by a mating shape effect.

When, curing movement of lever 48, spur 51 passes the first notch 52 which it meets in its path, clamping is such that pouch 40 may still be moved with respect to the pouch-holder, not for removal however, but by a rotation about its axis for example for modifying the position of said pouch with respect to the body of the user, or facilitating emptying, etc . . . when, on the other hand, the pivoting movement of lever 48 continues, until spur 51 passes over notch 53 or until, in the variant also illustrated, spur 51' passes over the bridge 34, then the clamping force is such that untimely separation of the pouch and the pouch-holder is impossible.

In this condition also the inner surface 66 of connection 62 cooperates with the external surface of end-piece 16 with creation of a linear contact zone 71, FIG. 5, which provides sealing between the end-piece and the pouch, which are further mechanically connected together.

A reverse procedure is used for separating the pouch 40 from the pouch-holder 10, after rotation of the pivoting lever 48 in the reverse direction to that shown by arrow f and after spur 51 has escaped from notch 53, or spur 51' from bridge 34, taking advantage, on the one hand, of the action of teeth 46 and 47 which cooperate together but also, on the other hand, from the resilient nature of the material forming member 24.

A contribution to the perfect safety of the appliance is also made by the fact that, because of the paired profiles of the connection or pouch nose 62 and member 24, actuation of lever 48 as far as the position in which its spur 51 cooperates with notch 53 or its spur 51' with bridge 34 is impossible as long as connection 62 is badly positioned in space 70, whereas if the positioning of said connection in said space is not satisfactory, but is close to this condition, the surface 41 of member 24 acts as a pusher on the connection for positioning it quite satisfactorily, previous to locking by clamping by means of lever 48.

Operation of the appliance is simple and reliable and very satisfactory operation has been obtained for an appliance comprising an end-piece 16 of 50 mm in diameter, a wall 22 of about 70 mm in diameter, a pouch nose of about 58 mm in external diameter and 52 mm internal diameter with a clamping member 24 having a width of about 5 mm, with two teeth with a primitive diameter of about 66 mm with which the mating teeth of the lever cooperate.

Figure 12:
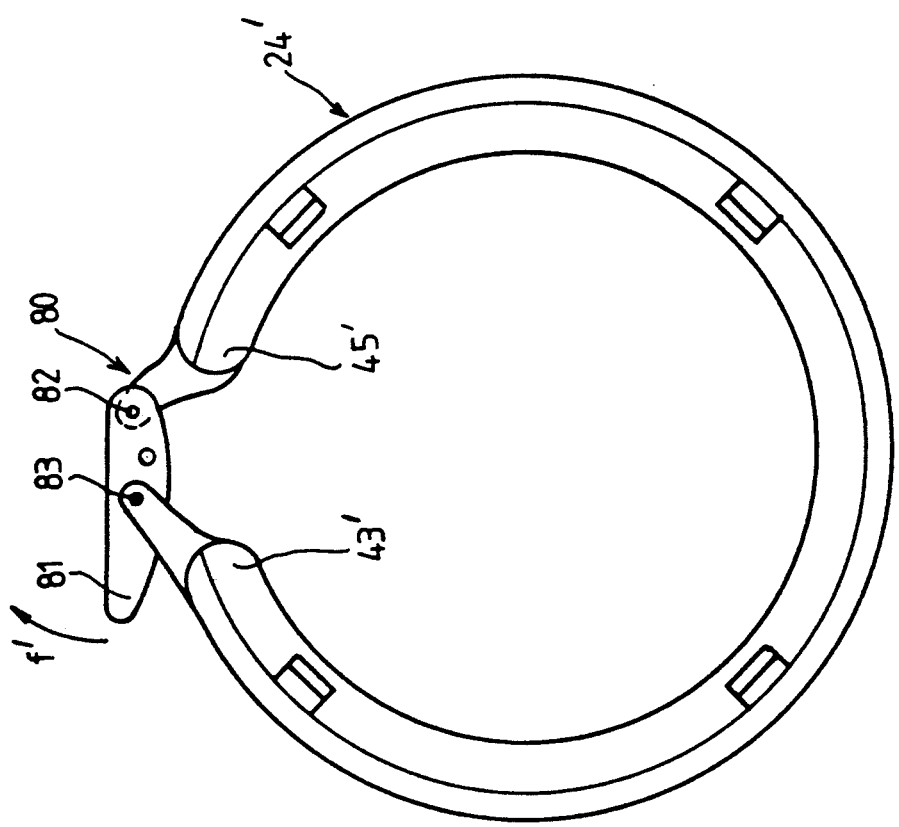
FIG. 12 illustrates a variant of construction.

The invention is not limited to the embodiment and application which have been described more explicitly. It embraces, on the contrary, all variants thereof which may occur to one skilled in the art. Thus, and as shown in FIG. 12, member 24' similar to member 24 of the preceding embodiment may have at its ends 43' and 45', distant from each other as long as the pouch is not fitted on the pouch-holder, an articulated lever mechanism 80, and lever 81 pivoting in the direction of arrow f' about an axis 82 for driving the end 43' articulated on the lever about an axis 83, for bringing end 45' nearer.

Figure 13:
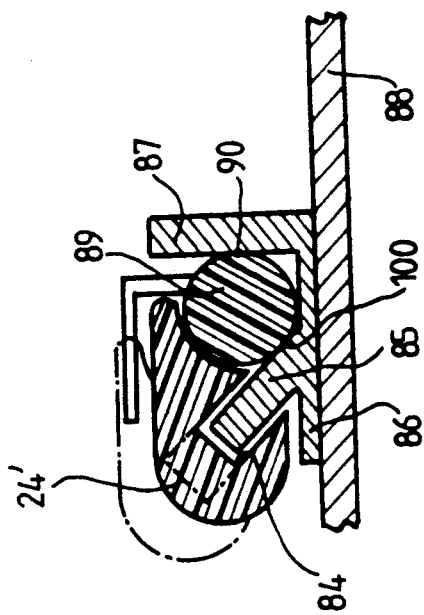
FIG. 13 is a sectional view illustrating another embodiment.

In such an appliance where the pouch-holder is shown schematically at 88, the cross section of member 24' may be as shown in FIG. 13, i.e. with a general triangular contour with a recess 84 for guiding on a rib 85 projecting from base 86 and extending radially outside an end-piece 87 similar to end-piece 16 of the preceding embodiment. In this embodiment, pouch nose 89, of a somewhat circular cross section, is positioned on the pouch-holder when member 24' is in the condition shown with a chain-dotted line in FIG. 13 and, when the articulated lever mechanism 80 or a similar mechanism is actuated, member 24' takes up its position shown with a continuous line in this figure for clamping said pouch nose which is immobilized by the mating shape effect between rib 85 and the external surface of end-piece 87 with, in such a construction, two linear sealing zones as shown schematically at 90 and 100.

What is claimed is:

1. An ostomy appliance, comprising:
   a pouch-holder with an end-piece for being fixed about a stoma opening in the body of a user so that said end-piece surrounds the stoma in its condition of use,
   a waste material collecting pouch adapted to be releasably secured with the pouch-holder by a nose of the pouch and which is provided for engaging said end-piece,
   a control mechanism for the appliance connected to the pouch-holder, and
   a deformable clamping member connected with the pouch-holder and which is separate from said control mechanism for cooperating directly and solely with the pouch nose, said clamping member including means for providing a sealed mechanical connection of said pouch nose with said end-piece in response to actuation of said control mechanism.

2. Appliance as claimed in claim 1, wherein said clamping member is a ring portion and the mechanism associated with the pouch-holder is adapted for bringing one of the ends of said member close to the other end from which it was initially remote.

3. Appliance as claimed in claim 2, wherein the pouch nose is made of molded plastic material made of one of an ethylene and vinyl acetate copolymer (EVA) and a compressible polymer polyurethane foam with an integrated surface skin.

4. Appliance as claimed in claim 2, wherein said clamping member comprises a rigid plastic material made from a material chosen among polypropylene, polyamide, ABS copolymer and high density polyethylene.

5. Ostomy appliance as claimed in claim 1, wherein the control mechanism for actuating the clamping member comprises articulated lever means for bringing initially distant ends of said member close together.

6. Appliance as claimed in claim 1, wherein the control mechanism for actuating the clamping member comprises an eccentric type mechanism for bringing the initially distant ends of said member close together.

7. Appliance as claimed in claim 1, wherein the control mechanism comprises a meshing actuating mechanism with teeth at one end of the clamping member and teeth of mating shapes provided on a lever mounted for pivoting on a part holding said member in position.

8. Appliance as claimed in claim 1, wherein sealing of a junction between the pouch nose and the end piece of the pouch-holder is provided by at least one linear type contact between the external surface of the pouch nose and said end piece.

9. Appliance as claimed in claim 8, wherein the surface of the end-piece with which the pouch nose cooperates has a truncated cone shape and that of said pouch nose is bellied or vice versa.

10. Appliance as claimed in claim 1, wherein the actuating mechanism comprises locking means.

11. Appliance as claimed in claim 1, wherein the cross section of the pouch nose and that of the clamping member are in mating engagement so that actuation of the control mechanism drawing ends of the clamping member close together is preventing when the pouch nose is not correctly positioned with respect to said clamping member and the end piece of the pouch-holder.

12. An ostomy appliance made of a plastic material and comprising:
 a pouch-holder having a relatively rigid end-piece; said end-piece being fixed about a stoma opening in the body of the user so that said end piece surrounds the stoma during use
 a flexible waste collecting ouch having a nose extending therefrom which is resiliently deformable and engageable within said end piece;
 a resiliently deformable clamping member connected with the pouch holder and acting by clamping action for immobilizing the pouch nose with respect to the end-piece by a mating shape effect; and
 a control mechanism for actuating said clamping member such that said clamping member provides a sealed mechanical connection of said pouch nose within said end-piece upon actuation of said control mechanism.

13. Pouch for collecting body waste and/or fluids, particularly for enterostomy or urostomy, entering into the construction of an appliance comprising: a pouch-holder with an end-piece for being fixed about a stoma opening in the body of a user so that said end-piece surrounds the stoma during use,
 a waste material collecting pouch adapted to be releasably secured with the pouch-holder by an annular nose of the pouch and which is provided for engaging said end-piece,
 a control mechanism for the appliance connected to the pouch-holder,
 a deformable clamping member connected to the pouch-holder and which is separate from said control mechanism for cooperating directly and solely with the pouch nose, said clamping member including means for providing a sealed mechanical connection of said pouch nose with said end-piece in response to actuation of said mechanism wherein the pouch nose comprises a flexible resiliently deformable material and whose cross section mates with that of the clamping ember, on the one hand, and is paired with the end-piece of the pouch-holder, on the other hand, to provide the sealed connection between the pouch and the pouch-holder.

14. Collecting pouch as claimed in claim 13, wherein the pouch nose comprises an EVA copolymer of polyurethane elastomer base.

15. Collecting pouch as claimed in claim 13, wherein the pouch nose comprises a cellular material with an integrated surface skin having one of an EVA copolymer and polyurethane elastomer base.

16. Collecting pouch as claimed in claim 13, wherein the pouch nose comprises a cellular material with integrated surface skin having of an EVA copolymer and a polyurethane base.

17. Pouch-holder for use with a pouch for collecting body waste and/or fluids, which comprises:
 an end-piece for being fixed about a stoma opening in the body of a user so that said end-piece surrounds the stoma during use;
 a control mechanism connected to the pouch-holder;
 a deformable clamping member connected to the pouch-holder which is separate from said control mechanism for cooperating directly and solely with a collecting pouch, said clamping member including means for providing a sealed mechanical connection of said pouch with said end-piece in response to actuation of said control mechanism.

18. Pouch-holder as claimed in claim 17, wherein said clamping member is held in position on said end-piece by being housed between a radial collar, external of the end-piece, and a wall with bent back portions directed substantially parallel to said collar.

19. Pouch-holder as claimed in claim 17, wherein said control mechanism comprises a pivoting lever having a set of teeth cooperating with teeth of mating shape formed on the external surface of the clamping member and wherein said lever is mounted for pivoting about an axis extending between two journals carried by the lever and which are engaged in eyes of mating shapes of two radially projecting cheeks of said end-piece.

20. Pouch-holder as claimed in claim 17, wherein said end-piece is shaped as a flange.

* * * * *